United States Patent
Aoyagi et al.

(10) Patent No.: US 8,548,546 B2
(45) Date of Patent: Oct. 1, 2013

(54) PULSE OXIMETRY AND PULSE OXIMETER

(75) Inventors: Takuo Aoyagi, Tokyo (JP); Michio Kanemoto, Tokyo (JP); Masayoshi Fuse, Tokyo (JP); Teiji Ukawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 666 days.

(21) Appl. No.: 12/486,843

(22) Filed: Jun. 18, 2009

(65) Prior Publication Data

US 2009/0318787 A1 Dec. 24, 2009

(30) Foreign Application Priority Data

Jun. 19, 2008 (JP) ................................. 2008-160013

(51) Int. Cl.
*A61B 5/00* (2006.01)

(52) U.S. Cl.
USPC .......................................... 600/323; 600/336

(58) Field of Classification Search
USPC ........................... 600/310, 322, 323, 326, 336
See application file for complete search history.

(56) References Cited

U.S. PATENT DOCUMENTS

| | | | | |
|---|---|---|---|---|
| 5,765,563 A * | 6/1998 | Vander Schaaf | ............... | 600/538 |
| 6,381,351 B1 * | 4/2002 | Powell | ........................... | 382/131 |
| 6,771,997 B2 * | 8/2004 | Schaffer | ........................ | 600/410 |
| 7,206,621 B2 | 4/2007 | Aoyagi et al. | | |
| 7,738,936 B1 * | 6/2010 | Turcott | ........................... | 600/339 |
| 8,126,528 B2 * | 2/2012 | Diab et al. | ..................... | 600/323 |

| | | | |
|---|---|---|---|
| 2004/0267140 A1 | 12/2004 | Ito et al. | |
| 2005/0049469 A1 | 3/2005 | Aoyagi et al. | |
| 2007/0049812 A1 | 3/2007 | Aoyagi et al. | |
| 2008/0033266 A1 | 2/2008 | Diab et al. | |

FOREIGN PATENT DOCUMENTS

| | | | |
|---|---|---|---|
| JP | 07-327964 A | 12/1995 | |
| JP | 2004-202190 A | 7/2004 | |
| JP | 2005-95606 A | 4/2005 | |
| JP | 2007-90047 A | 4/2007 | |

OTHER PUBLICATIONS

European Search Report dated Aug. 21, 2009.
Office Action issued Jun. 29, 2012 by the Japanese Patent Office in counterpart Japanese Reference No. 2008-160013.
Official Communication in corresponding European Patent Application No. 09 162 886.7-1660 dated Mar. 12, 2013.
Mode (statistics):, Wikikpedia, URL:HTTP://en.wikipedia.org/w/index.php$title=Mode_%28statistics%29&oldid=213470577; May 19, 2008.

* cited by examiner

*Primary Examiner* — Christopher Mahoney
(74) *Attorney, Agent, or Firm* — Sughrue Mion, PLLC

(57) ABSTRACT

A pulse oximetry includes: irradiating living tissue with a plurality of light beams of different wavelengths; receiving the light beams transmitted through or reflected from the living tissue and converting the received light beams to electric signals which correspond to the different wavelengths; time-segmenting time series data of the electric signals; calculating, with respect to each of the segmented time series data of the electric signals, a slope value of a regression line between each two of the electric signals; calculating SaO2 based on the slope value of each of the segmented time series data of the electric signals; constructing a histogram of SaO2 for each predetermined number of time segments; and obtaining a mode value from the histogram as SpO2 to be output of the pulse oximetry.

5 Claims, 3 Drawing Sheets

PULSE OXIMETRY AND PULSE OXIMETER

BACKGROUND OF THE INVENTION

The present invention relates to a pulse oximetry which measures continuously arterial oxygen saturation (SaO2) in a non-invasive manner by using a blood volume variation of the tissue arterial blood caused by pulsation, and also to a pulse oximeter which performs such a pulse oximetry.

Today, in a related-art technique called a pulse oximetry, in the case where SaO2 is to be obtained, the following procedure is usually adopted.

(1) Tissue transmitted or reflected light is continuously measured at a plurality of wavelengths.
(2) The peak and bottom of pulsation of the measured tissue transmitted or reflected light are determined, and the transmitted or reflected light beams at the peak and bottom are indicated by L+ΔL and L, respectively.
(3) $\Delta A \equiv \log[(L+\Delta L)/L] \approx \Delta L/L$ is obtained.
(4) $\Phi ij \equiv \Delta Ai/\Delta Aj$ is obtained.
(5) Since Φij corresponds on a substantially one-to-one base to SaO2, Φij is converted to SaO2.

Many apparatuses which are currently commercially available, and which measure SaO2 employ two wavelengths, and, when above-described Φij is to be converted to SaO2, use a conversion table. In the case of a two-wavelength apparatus, the use of a conversion table is not particularly problematic. In the case where a larger number of wavelengths are used in order to improve the measurement accuracy, however, the conversion must be performed by using a calculation expression which is obtained theoretically and experimentally.

For example, as a related-art apparatus which measures continuously SaO2 in a non-invasive manner by using a volume variation of arterial blood caused by pulsation, there is a five-wavelength pulse oximeter which irradiates living tissue with five light beams of different wavelengths (see JP-A-2005-95606).

The pulse oximeter disclosed in JP-A-2005-95606 includes: a light emitting portion which irradiates living tissue with five light beams of different wavelengths; a light receiving portion which receives the light beams that are emitted from the light emitting portion, and that are transmitted through or reflected from the living tissue, and which converts the light beams to electric signals; an optical-density-variation calculating portion which obtains optical density variations for the living tissue on the basis of variations of the transmitted or reflected light beams of different wavelengths and output from the light receiving portion; an optical-density-variation-ratio calculating portion which obtains at least four of mutual ratios of five optical density variations obtained in the optical-density-variation calculating portion; and an oxygen saturation calculating portion which, based on the optical-density-variation ratios obtained in the optical-density-variation-ratio calculating portion, calculates oxygen saturation in blood while using four unknowns of the SaO2, the venous oxygen saturation, a ratio of variations of arterial blood and venous blood, and a tissue term, and obtains oxygen saturation of arterial blood while eliminating artifacts of variations of venous blood and the tissue.

According to the thus configured pulse oximeter disclosed in JP-A-2005-95606, in the case where venous blood is pulsated by any reason, an artifact of the pulsation can be surely eliminated, and SaO2 can be accurately measured without producing a time delay and smoothing. In the case where the pulse wave is so small that a pulse oximetry is impossible, body motion is intentionally applied, thereby enabling SaO2 contained in this case to be obtained. The pulse oximeter has another advantage that also venous oxygen saturation can be simultaneously measured.

A longstanding problem of a pulse oximetry is that transmitted or reflected light is disturbed by mechanical disturbances such as body motion. Namely, disturbances of transmitted or reflected light cause adequate detection of peaks and bottoms of a measured pulsative waveform to be hardly performed.

A related-art technique which has been proposed or adopted as a countermeasure against these problems is a statistical technique in which the correct value of SaO2 is estimated from preceding and subsequent data. However, the technique has the following problems.

(1) Since a long time delay is produced, detection of, for example, a start of reduction of SaO2 is delayed.
(2) Changes of SaO2 are smoothed. When SaO2 is largely reduced, for example, the degree of the reduction cannot be known.

In the related-art pulse oximetry technique, it will be further expected that a change in SaO2 of a patient is quickly detected, so that the change is early coped with. In order to utilize the original feature of the pulse oximetry technique, the above-discussed problems must be solved.

Furthermore, it has been found that, in the related-art pulse oximetry technique which is based on determination of peaks and bottoms of the pulsative waveform of measured transmitted or reflected light cannot obtain a satisfactory measurement result when the body a patient is vigorously moved.

From this viewpoint, the following related-art technique has been proposed, a time-segmented pulse oximetry and pulse oximeter in which, with respect to the pulsative waveform of measured transmitted or reflected light, the whole of a signal of the measured transmitted or reflected light is used, whereby SaO2 can be adequately measured (see JP-A-2007-90047).

In the related-art technique disclosed in JP-A-2007-90047, the whole of time series data of the transmitted or reflected light is used, so that determination of peaks and bottoms of the measured waveform is not necessary. Namely, the related-art technique disclosed in JP-A-2007-90047 is characterized in that light emitting elements irradiate living tissue with a plurality of light beams of different wavelengths, light receiving elements receive the light beams transmitted through or reflected from the living tissue, and converts the respective light beams to electric signals, time series data of the electric signals obtained by the light receiving elements are time-segmented, with respect to the segmented time series data, slope values of regression lines between two different wavelengths are calculated, the calculated slope values are converted to SaO2, respectively, and then smoothing is performed, thereby obtaining SaO2 from which an artifact of body motion is eliminated.

According to the related-art technique disclosed in JP-A-2007-90047, with respect to the pulsative waveform of measured transmitted or reflected light, therefore, determination of peaks and bottoms of the measured waveform is not performed, and the whole of time series data of the transmitted or reflected light is used, whereby an artifact of body motion is eliminated, contribution to improvement of the measurement accuracy of SaO2 is obtained, and measurement flexibility of a measurement portion can be enhanced. Even with these two related-art techniques, an artifact of the body motion can not be eliminated sufficiently.

SUMMARY

It is therefore an object of the invention to provide a pulse oximetry and pulse oximeter in which, with respect to the pulsative waveform of measured transmitted or reflected light, the whole of time series data of the transmitted or reflected light is used, whereby an artifact of body motion is eliminated, and contribution to further improvement of the measurement accuracy of SaO2 is obtained.

In order to achieve the object, according to the invention, there is provided a pulse oximetry comprising:

irradiating living tissue with a plurality of light beams of different wavelengths;

receiving the light beams transmitted through or reflected from the living tissue and converting the received light beams to electric signals which correspond to the different wavelengths;

time-segmenting time series data of the electric signals;

calculating, with respect to each of the segmented time series data of the electric signals, a slope value of a regression line between each two of the electric signals;

calculating SaO2 based on the slope values of each of the segmented time series data of the electric signals;

constructing a histogram of SaO2 for each predetermined number of time segments; and obtaining a mode value from the histogram as SpO2 to be output of the pulse oximetry.

The time series data of the electric signals may be passed through a filter to block a low-frequency component, before time-segmenting the time series data of the electric signals.

The pulse oximetry may further include: calculating, with respect to each of the segmented time series data of the electric signals, correlation between each two of the electric signals. When the correlation is less than a predetermined value, the slope value which corresponds to the correlation may be deleted.

A smoothing process may be applied to the histogram of the SaO2, before obtaining the mode value.

In order to achieve the object, according to the invention, there is also provided a pulse oximeter comprising:

a light emitter, which irradiates living tissue with a plurality of light beams of different wavelengths;

a light receiver, which receives the light beams transmitted through or reflected from the living tissue and which converts the received light beams to electric signals which correspond to the different wavelengths;

a processor, which segments time series data of the electric signals;

a slope value calculator, which calculates, with respect to each of the segmented time series data of the electric signals, a slope value of a regression line between each two of the electric signals;

an SaO2 calculator, which calculates SaO2 based on the slope value of each of the segmented time series data of the electric signals;

a histogram constructer, which constructs a histogram of SaO2 for each predetermined number of time segments; and an obtainer, which obtains a mode value from the histogram as SpO2 to be output of the pulse oximeter.

DETAILED DESCRIPTION OF EMBODIMENTS

Next, an embodiment of a pulse oximetry of the present invention will be described in relation with the configuration of a pulse oximeter which performs the pulse oximetry, in detail with reference to the accompanying drawings.

I. Summary of Configuration of Pulse Oximeter

Figure 1:
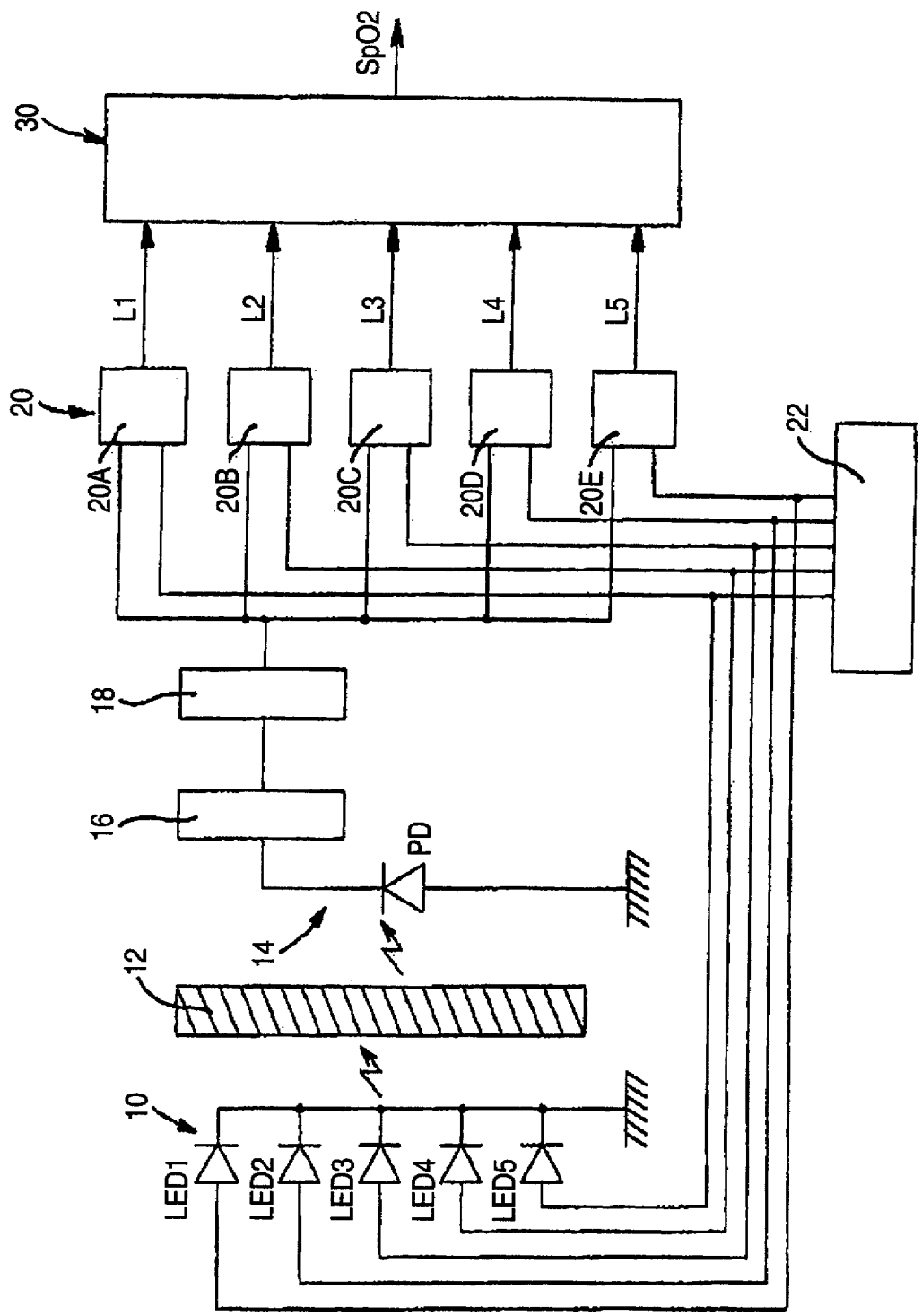
FIG. 1 is a diagram schematically showing the configuration of a pulse oximeter which performs a pulse oximetry of the present invention.

FIG. 1 is a diagram schematically showing the configuration of a pulse oximeter which performs a pulse oximetry of the present invention. In FIG. 1, the reference numeral 10 denotes a light emitting portion in which five light emitting elements LED1 to LED5 that irradiate living tissue with five light beams of different wavelengths, respectively, 12 denotes the living tissue which is irradiated with the light beams emitted from the light emitting portion 10, and 14 denotes a light receiving portion configured by: a light receiving element PD which receives light beams transmitted through or reflected from the living tissue 12; a current-voltage converter 16; and an AD converter 18.

The reference numeral 20 denotes a storage portion configured by transmitted-light-signal temporary storage devices 20A to 20E which temporarily store transmitted or reflected light signals obtained by the light receiving element PD of the light receiving portion 14, in time series for the respective wavelengths. For example, 60 transmitted or reflected light signals are stored per second in each of the storage devices.

The reference numeral 30 denotes a calculating portion which, on the basis of the transmitted or reflected light signals L1 to L5 that are temporarily stored in time series in the respective transmitted-light-signal temporary storage devices 20A to 20E, performs the following procedures: (1) the transmitted or reflected light signals L1 to L5 are segmented for each predetermined time; (2) with respect to each of the transmitted or reflected light signals L1 to L5 which are segmented for each predetermined time, then, a slope value of a regression line between each two different wavelengths is calculated; (3) SaO2 is calculated based on the calculated slope values; (4) a correlation coefficient is further calculated, a slope value in the case where the correlation coefficient is less than a predetermined value is deleted, and a histogram of SaO2 is constructed for every predetermined number of time segments; and (5) a mode value of the histogram is set as an SpO2 value.

The reference numeral 22 denotes a timing device which is configured so as to control light emitting timings of the light emitting elements LED1 to LED5 of the light emitting portion 10, and timings of storing the transmitted or reflected light signals in the transmitted-light-signal temporary storage devices 20A to 20E of the storage portion 20.

Figure 2:
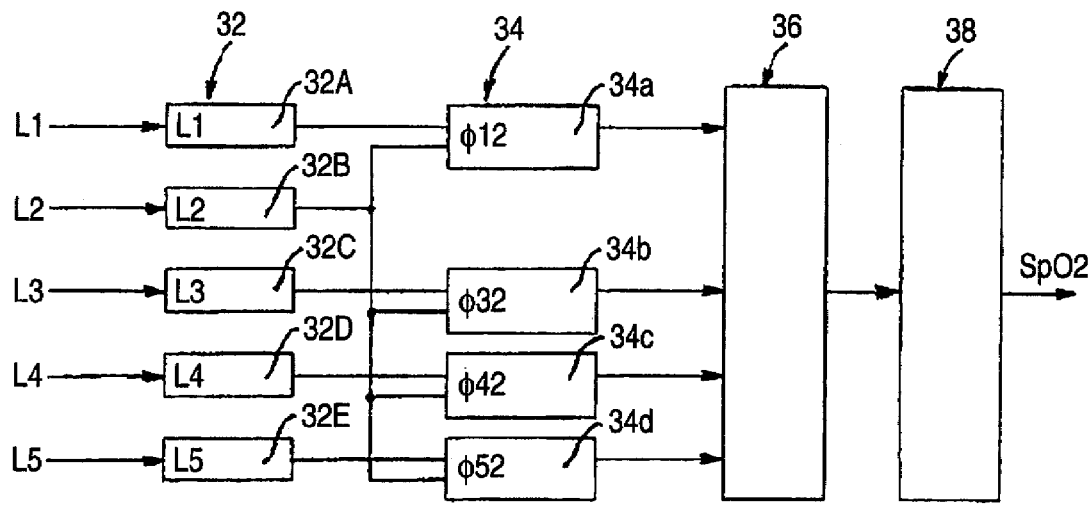
FIG. 2 is a diagram showing the configuration of a system in a calculating portion of the pulse oximeter shown in FIG. 1.

FIG. 2 is a diagram showing the configuration of a system for performing the above-described calculating procedures in an oxygen saturation calculator that functions as the calculating portion 30. In FIG. 2, the reference numeral 32 denotes a segment storage portion for the transmitted or reflected light signals. The segment storage portion is configured by segment storing circuits 32A to 32E which segment the transmitted or reflected light signals L1 to L5 supplied from the transmitted-light-signal temporary storage devices 20A to 20E, for each predetermined time (for example, 0.2 second), and which sequentially store the transmitted or reflected light signals in time series for each of the segmented times.

The reference numeral 34 denotes a slope-value calculating portion. The calculating portion is configured by slope-value calculating circuits 34a, 34b, 34c, 34d calculate, using output of 32, slope values $\Phi 12$, $\Phi 32$, $\Phi 42$, $\Phi 52$ of the regression lines, respectively.

The reference numeral 36 denotes a first calculating circuit which obtains the SaO2 value as a solution of simultaneous equations with the slope values $\Phi 12$, $\Phi 32$, $\Phi 42$, $\Phi 52$ of the regression lines that are obtained by the slope-value calculating circuits 34a, 34b, 34c, 34d. The value which is the solution of simultaneous equations obtained by the first calculating circuit is called 5wSall.

The reference numeral 38 denotes a second calculating circuit which, with respect to SaO2 that is obtained as the solution of the simultaneous equations, obtains a histogram for every predetermined number of time segments (for example, every 5 seconds), and which determines the mode value of the histogram. Therefore, the second calculating circuit 38 calculates blood oxygen saturation [SpO2]. This is output of this pulse oximetry.

In order to obtain a higher accuracy, it is preferred to additionally perform at least one of the following methods.
<1> a low-frequency component of log Li is eliminated.
<2> $\Phi i2$ is selected based on correlation between two data.
<3> Smoothing is performed on the histogram.

II. Calculating Processing of Pulse Oximeter

Next, the operation of calculating SaO2 by the configuration of the above-described pulse oximeter, i.e., the pulse oximetry of the invention will be described together with the function of the pulse oximeter.

(1) Processing of Time-Segmenting Transmitted or Reflected Light Signal

First, the five light emitting elements LED1 to LED5 of the light emitting portion 10 sequentially emit light beams of different wavelengths $\lambda 1$, $\lambda 2$, $\lambda 3$, $\lambda 4$, and $\lambda 5$, respectively, on the basis of a signal from the timing device 22. Therefore, the light receiving portion 14 receives light beams transmitted through or reflected from the living tissue 12, and, in accordance with the wavelengths of the light emitting elements LED1 to LED5, the transmitted or reflected light signals L1, L2, L3, L4, L5 are stored at respective predetermined timings into the transmitted-light-signal temporary storage devices 20A to 20E of the storage portion 20 (see FIG. 1).

The transmitted or reflected light signals L1 to L5 which are stored respectively in the transmitted-light-signal temporary storage devices 20A to 20E in this way are supplied to the segment storing circuits 32A to 32E of the segment storage portion 32 in the calculating portion 30, segmented for each predetermined time (for example, 0.2 second), and then sequentially stored in time series for each of the segmented times (see FIG. 2).

(2) Calculating Processing of Obtaining Slope Value of Regression Line Relating to Time-Segmented Transmitted or Reflected Light Beams The calculation of blood oxygen saturation (SpO2) is performed based on optical density variations ($\Delta Ai$) which are obtained for the transmitted or reflected light beams of, for example, five wavelengths. The oxygen saturation is obtained by the following expression using a ratio ($\Phi ij$, i and j are wavelength number) of the optical density variations.

The elements constituting the pulsation of a transmitted or reflected light beam are arterial blood (a), venous blood (v), and tissue other than blood, i.e., pure tissue (t).

$$\Phi ij \equiv \Delta Ai/\Delta Aj$$
$$= [\sqrt{Eai(Eai+F)} + \sqrt{Evi(Evi+F)} * V + Exi]$$
$$/ [\sqrt{Eaj(Eaj+F)} + \sqrt{Evj(Evj+F)} * V + Exj]$$

where $$\Delta Ai \equiv \log[(Li+\Delta Li)/Li] \cong \Delta Li/Li$$

$$Eai \equiv SaEoi + (1-Sa)Eri$$

$$Evi \equiv SvEoi + (1-Sv)Eri$$

$$V \equiv \Delta Dv/\Delta Da$$

$$Exi \equiv Zti\Delta Dt/(Hb\Delta Da) \equiv AiEx2 + Bi$$

In the above expression, Li is a tissue transmitted or reflected light beam, $\Delta Ai$ is an optical density variation, Eoi is an extinction coefficient of oxygenated hemoglobin, Eri is an extinction coefficient of deoxygenated hemoglobin, Sa is SaO2, Sv is oxygen saturation of peripheral venous blood (SvO2), $\Delta Da$ is a variation of the effective thickness of arterial blood, $\Delta Dv$ is a variation of the effective thickness of venous blood, $\Delta Dt$ is a variation of the effective thickness of pure tissue, Zti is a constant of attenuation of pure tissue, Ex2 is the value of Exi at a second wavelength, and Ai and Bi are tissue constants (determined by actual measurement).

Therefore, the above expression has four unknowns of Sa, Sv, V, and Ex2.

In this case, tissue transmitted or reflected light beams are measured at five adequate wavelengths, simultaneous equations with 4 unknowns are set with respect to the above expression, and then Sa can be obtained as the solution of the simultaneous equations. Preferred examples of the five wavelengths are $\lambda 1=805$ nm, $\lambda 2=875$ nm, $\lambda 3=660$ nm, $\lambda 4=700$ nm, and $\lambda 5=730$ nm.

In the time-segmented oximetry of the invention, based on the transmitted or reflected light signals L1 to L5 of the five wavelengths ($\lambda 1$ to $\lambda 5$) which are time-segmented and stored, therefore, the segment storage portion 32 obtains the slope values ($\Phi ij$, i and j are wavelength number) of the regression lines by using the following expression. Namely, the slope value ($\Phi ij$) in the above corresponds to $\Phi ij = \Delta Ai/\Delta Aj$ above. In the following expression, n is the number of data in a time segment, t is a segmented time (for example, 0.2 second), and $\Sigma$ is a sum of data in a segmented time.

$$\Phi ij = \{n\Sigma[Li(t)*Lj(t)] - \Sigma[Li(t)*\Sigma Lj(t)]\} / \{n\Sigma Lj(t)^2 - [\Sigma Lj(t)]^2\}$$

(3) Calculating Processing of Obtaining Solution of Simultaneous Equations with Slope Values On the basis of the above expression, simultaneous equations with 4 unknowns are set with respect to the slope values ($\Phi 12$, $\Phi 32$, $\Phi 42$, $\Phi 52$) of the regression lines for the tissue transmitted or reflected light beams of the five wavelengths ($\lambda 1$ to $\lambda 5$), and Sa is calculated as a solution of the simultaneous equations (see FIG. 2). These Sa are named 5wSall.

III. Example of Calculating Processing

An example where, based on the above-described pulse oximetry of the invention, SaO2 is calculated with respect to actual measurement data of a subject will be described together with graphs in which the example is compared with the case of a related-art pulse oximetry, and which show their measurement results.

The light emitting portion 10 and the light receiving portion 14 are attached to a finger tip of a subject, and breathing is performed in the following manner.

<1> Air breathing is performed.
<2> SaO2 is reduced by holding breath.
<3> Air breathing is again performed.
<4> SaO2 is increased by oxygen breathing.

In the middle of <1>, a motion of squeezing a sponge by hand is performed. The body motion is continued to the middle of <4>.

Similarly, a light emitting portion and a light receiving portion are attached to the other hand opposite to the one which performs the body motion. The other hand is kept at rest, and data of the other hand are set as control data.

Figure 3:
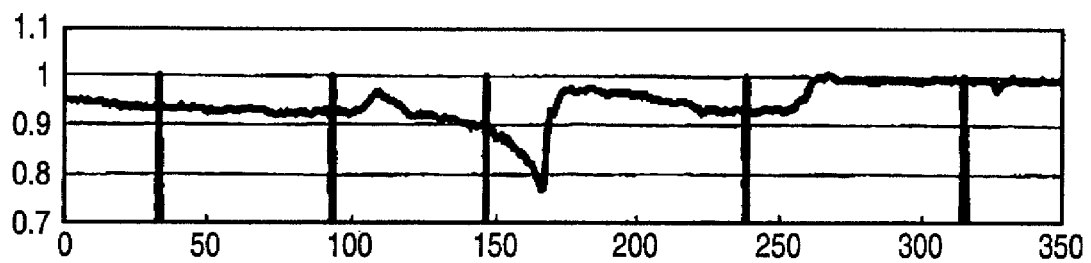
FIG. 3 is a waveform chart showing a change of SpO2 which is obtained in a rest side by a five-wavelength calculation while peaks and bottoms are determined for each beat.

FIG. 3 shows a result of SpO2 which is obtained in the rest side by a five-wavelength calculation while peaks and bottoms are determined for each beat. In FIG. 3, a change of SaO2 due to a change of breathing is clearly shown. In the graph, timings when breathing is changed and the body motion is started and ended are indicated by vertical bars.

Figure 4:
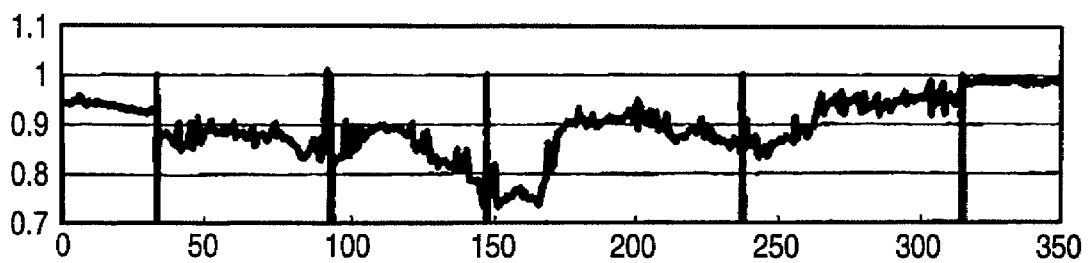
FIG. 4 is a waveform chart showing a change of SpO2 which is obtained in a body-motion side by the five-wavelength calculation while peaks and bottoms are determined for each beat.

FIG. 4 shows a result of SpO2 which is obtained in the body-motion side by a five-wavelength calculation while peaks and bottoms are determined for each beat. In FIG. 4, SpO2 is largely disturbed. This disturbance is caused by the artifact of the body motion.

Figure 5:
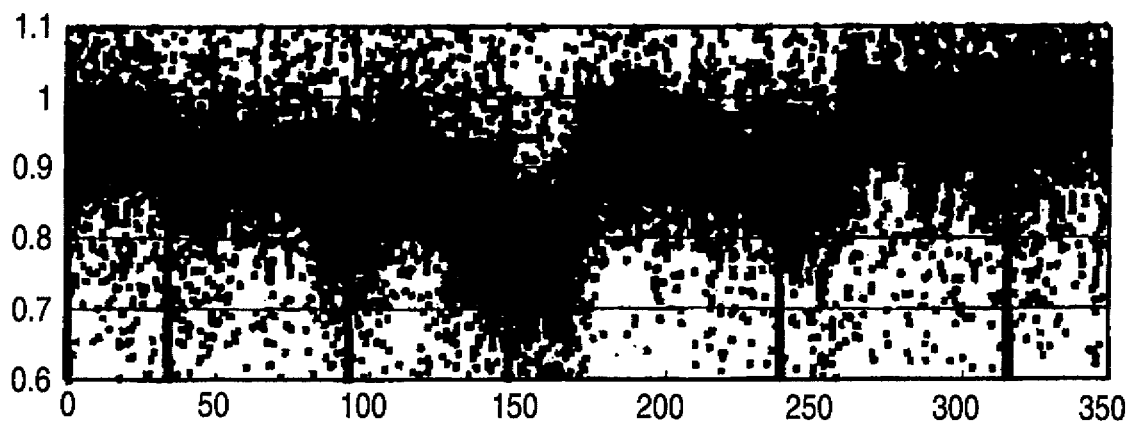
FIG. 5 is a waveform chart showing a change of 5wSall which is obtained in the body-motion side for each time segment.

FIG. 5 shows the distribution characteristic of 5wSall which is obtained in the body-motion side for each 0.2 second by the method of the invention. Namely, FIG. 5 is a view showing results of the following processing.

Figure 6:
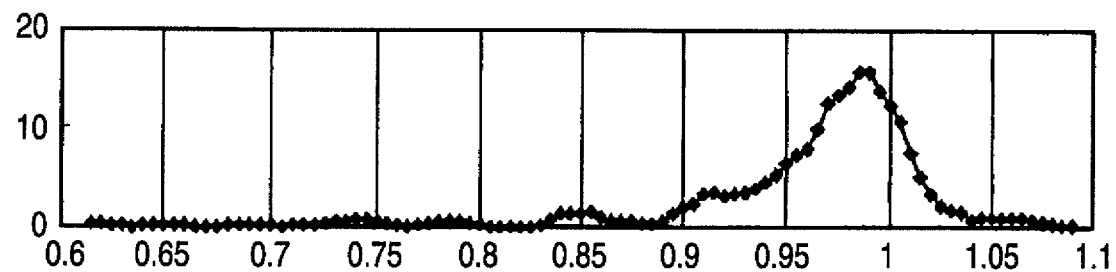
FIG. 6 is a waveform chart showing a display example of a histogram in the pulse oximetry of the invention.
Figure 7:
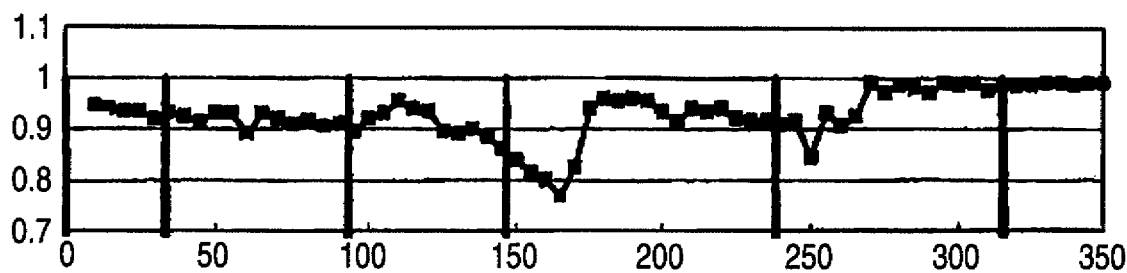
FIG. 7 is a waveform chart showing a change of SpO2 which is obtained in the body-motion side by the pulse oximetry of the invention.

<1> The transmitted or reflected light signal Li is logarithmically converted to log Li.
<2> A low-frequency component of log Li is eliminated. Specifically, the average value of log Li for each 0.1 second is subtracted from log Li.
<3> For each 0.2 second, a slope $\Phi i2$ of a regression line of log Li (i=1, 3, 4, and 5) and log L2 is obtained.
<4> For each 0.2 second, a correlation coefficient Ri2 of log Li (i=1, 3, 4, and 5) and log L2 is obtained, and R12*R32*R42*R52=PR is obtained.
<5> $\Phi i2$ in the case of PR<0.9 is deleted.
<6> The remaining $\Phi i2$ is converted to SaO2 on the basis of simultaneous equations. This is 5wSall.
<7> 5wSall is time-segmented for each 5 seconds, and a histogram of time segments of 5 seconds is obtained.
<8> The histogram is smoothed. FIG. 6 shows a display example of such a histogram.
<9> The mode value is determined on the basis of the histogram of 5wSall.
<10> The result is output as SpO2. FIG. 7 shows a change of SpO2 which is obtained in the body-motion side.

As described above, according to the pulse oximetry of the invention, an artifact of body motion is sufficiently eliminated, and a rapid change of SaO2 is definitely measured. Particularly, it is confirmed that the timing when the reduction of SaO2 is started can be detected without delay.

In the above, the preferred embodiment of the invention has been described. However, the invention is not restricted to the embodiment. Although the case where five wavelengths are used has been described, the invention can be applied also to the case where the number of wavelengths is larger or smaller than five. Furthermore, the invention can be applied also to all of measurement objects which pulsate, for instance, together with arterial blood, such as CO hemoglobin in blood, the diluted state of a dye injected from the outside of the body, etc. The interval of the time segment may be adequately changed in accordance with the respective objects. Various modifications may be performed without departing from the spirit of the invention.

According to an aspect of the invention, with respect to the pulsative waveform of measured transmitted or reflected light, determination of peaks and bottoms of the measured waveform is not performed, and the whole of time series data of the transmitted or reflected light is used, whereby an artifact of body motion is eliminated, and contribution to improvement of the measurement accuracy of SaO2 is obtained.

What is claimed is:

1. A pulse oximetry method comprising:
   irradiating living tissue with light beams of at least five wavelengths which are different from each other;
   receiving the light beams transmitted through or reflected from the living tissue and converting the received light beams to electric signals which correspond to the at least five wavelengths;
   time-segmenting time series data of the electric signals;
   calculating, with respect to each of the segmented time series data of the electric signals, a slope value of a regression line between each two of the electric signals;
   calculating an arterial oxygen saturation, SaO2, based on the slope values of each of the segmented time series data of the electric signals, by using an expression obtained in consideration of an effect related to tissue and venous blood;
   constructing a histogram of SaO2 for each predetermined number of time segments; and
   obtaining a mode value from the histogram as a measured value of SaO2 to be output of the pulse oximetry.

2. The pulse oximetry method according to claim 1, wherein
   the time series data of the electric signals are passed through a filter to block a low-frequency component, before time-segmenting the time series data of the electric signals.

3. The pulse oximetry method according to claim 1, further comprising:
   calculating, with respect to each of the segmented time series data of the electric signals, correlation between each two of the electric signals,
   wherein, when the correlation is less than a predetermined value, the slope value which corresponds to the correlation is deleted.

4. The pulse oximetry method according to claim 1, wherein a smoothing process is applied to the histogram of the SaO2, before obtaining the mode value.

5. A pulse oximeter comprising:
   a light emitter, which irradiates living tissue with light beams of at least five wavelengths which are different from each other;
   a light receiver, which receives the light beams transmitted through or reflected from the living tissue and which converts the received light beams to electric signals which correspond to the at least five wavelengths;
   a processor, which segments time series data of the electric signals;
   a slope value calculator, which calculates, with respect to each of the segmented time series data of the electric signals, a slope value of a regression line between each two of the electric signals;
   an SaO2 calculator, which calculates an arterial oxygen saturation, SaO2, based on the slope values of each of the segmented time series data of the electric signals, by using an expression obtained in consideration of an effect related to tissue and venous blood;

a histogram constructer, which constructs a histogram of SaO2 for each predetermined number of time segments; and a mode value obtainer, which obtains a mode value from the histogram as a measured value of SaO2 to be output of the pulse oximeter.

\* \* \* \* \*